United States Patent
Osaka et al.

(10) Patent No.: US 9,977,059 B2
(45) Date of Patent: May 22, 2018

(54) ELECTROCHEMICAL ANALYSIS APPARATUS AND ELECTROCHEMICAL SYSTEM

(71) Applicant: WASEDA UNIVERSITY, Tokyo (JP)

(72) Inventors: Tetsuya Osaka, Tokyo (JP); Toshiyuki Momma, Tokyo (JP); Tokihiko Yokoshima, Tokyo (JP); Daikichi Mukoyama, Tokyo (JP); Hiroki Nara, Tokyo (JP)

(73) Assignee: WASEDA UNIVERSITY, Tokyo (JP)

( * ) Notice: Subject to any disclaimer, the term of this patent is extended or adjusted under 35 U.S.C. 154(b) by 362 days.

(21) Appl. No.: 14/758,052

(22) PCT Filed: Dec. 26, 2013

(86) PCT No.: PCT/JP2013/084877
§ 371 (c)(1),
(2) Date: Jun. 26, 2015

(87) PCT Pub. No.: WO2014/104188
PCT Pub. Date: Jul. 3, 2014

(65) Prior Publication Data
US 2016/0195577 A1   Jul. 7, 2016

(30) Foreign Application Priority Data

Dec. 27, 2012   (JP) .................................. 2012-285550

(51) Int. Cl.
*G01N 27/416* (2006.01)
*G01R 23/16* (2006.01)
(Continued)

(52) U.S. Cl.
CPC ............. *G01R 23/16* (2013.01); *G01N 27/28* (2013.01); *G01N 27/4161* (2013.01); *G01R 31/3662* (2013.01); *H01M 10/48* (2013.01)

(58) Field of Classification Search
CPC . H01M 10/4285; H01M 10/48–10/486; G01N 27/3273; G01N 27/416; G01N 27/4161; G01N 27/026
See application file for complete search history.

(56) References Cited

U.S. PATENT DOCUMENTS 4,947,130 A    8/1990   Kitayoshi

FOREIGN PATENT DOCUMENTS

| EP | 0 321 963 A1 | 6/1989 |
| JP | 1-167679 A | 7/1989 |

(Continued)

OTHER PUBLICATIONS

JPO computer-generated English language translation of Kudo et al. JP 09-232005 A. Downloaded Aug. 17, 2017.*

(Continued)

*Primary Examiner* — Alexander S Noguerola
(74) *Attorney, Agent, or Firm* — Scully, Scott, Murphy & Presser, P.C.

(57) ABSTRACT

An electrochemical analysis apparatus 1 includes a power controller 20 that generates a rectangular wave signal having a first frequency (f1) and applies the rectangular wave signal to an electrochemical cell 10 including a plurality of electrodes 11 to 13 and an electrolyte 14, a Fourier transform section 30 that Fourier-transforms a response signal of the electrochemical cell 10 to the rectangular wave signal and calculates frequency characteristics including a component of a second frequency f2 of an integer multiple of the first frequency f1, and a calculating section 40 that calculates an impedance characteristic of the electrochemical cell 10 based on the frequency characteristics calculated by the Fourier transform section 30.

8 Claims, 10 Drawing Sheets

(51) Int. Cl.
*G01R 31/36* (2006.01)
*G01N 27/28* (2006.01)
*H01M 10/48* (2006.01)

(56) References Cited

FOREIGN PATENT DOCUMENTS

| | | | | |
|---|---|---|---|---|
| JP | 09-232005 A | * | 2/1996 | ............ H01M 10/48 |
| JP | 2002-330752 A | | 11/2002 | |
| JP | 2003-90869 A | | 3/2003 | |
| JP | 2005-180927 A | | 7/2005 | |
| JP | 2010-156702 A | | 7/2010 | |
| JP | 2012-15932 A | | 1/2012 | |
| JP | 2012-185167 A | | 9/2012 | |

OTHER PUBLICATIONS

Zhang et al., "Novel Kinetic and Background Current Selectivity in the Even Harmonic Components of Fourier Transformed Square-Wave Voltammograms of Surface-Confined Azurin," J. Phys. Chem. B 2005, 109, 8935-8947.*
"Battery Basics—How Do Lead Acid Batteries Work?" at the Service Department website for Progressive Dynamics, Inc Downloaded Aug. 17, 2017 from https://www.progressivedyn.com/battery_basics.html.*
JPO computer-generated English language translation of JP 2005-180927 A. Downloaded Aug. 17, 2017.*
International Search Report issued in PCT/JP2013/084877 dated Mar. 18, 2014 (in English and Japanese).

* cited by examiner

ELECTROCHEMICAL ANALYSIS APPARATUS AND ELECTROCHEMICAL SYSTEM

TECHNICAL FIELD

The present invention relates to an electrochemical analysis apparatus that measures characteristics of an electrochemical cell including a plurality of electrodes and an electrolyte and an electrochemical system including the electrochemical analysis apparatus.

BACKGROUND ART

Impedance measurement of an electrochemical cell including a plurality of electrodes and an electrolyte is widely used for, for example, clarification of a mechanism of an electrochemical reaction. As an impedance measurement method, an alternating-current impedance method for scanning a frequency of a sine wave signal applied to a measurement target electrochemical cell is known.

In the alternating-current impedance method, a frequency response analyzer (FRA) and a potentiostat are used. The FRA outputs a frequency response signal for applying a sine wave signal having a predetermined frequency to an electrochemical cell. The potentiostat controls, based on a frequency signal from the FRA, a voltage (an electric current) applied to the electrochemical cell.

By scanning the frequency having the sine wave signal, impedances at a plurality of frequencies, that is, a frequency characteristic of the impedance is acquired. A track of the impedance representing the frequency characteristic of the impedance in a complex plan view in which a Z' (real number impedance) axis represents a resistance component and a Z" (imaginary number impedance) axis represents a reactance component (usually, capacitive) is a Nyquist plot (a Cole-Cole plot).

Figure 1:
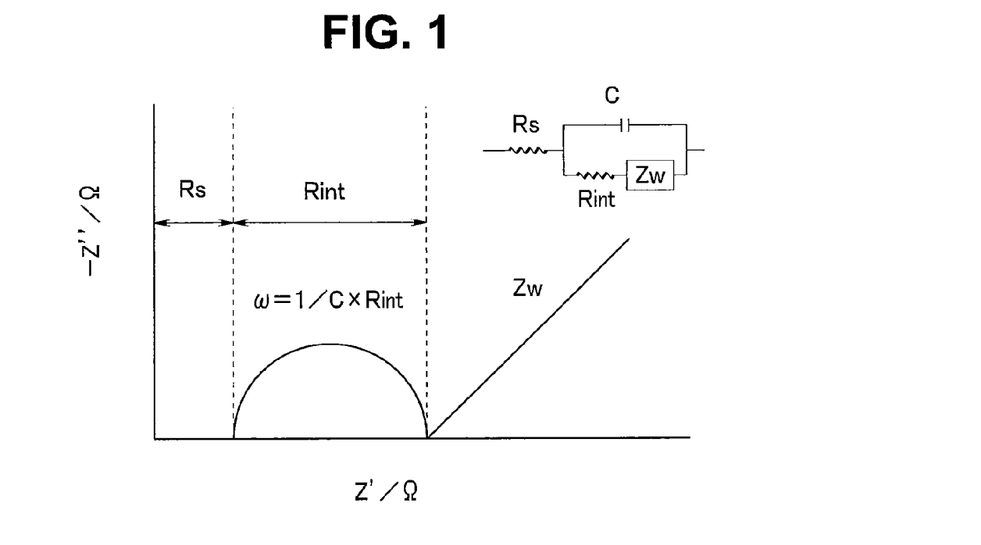
FIG. 1 is a diagram showing an example of a Nyquist plot.

The Nyquist plot shown in FIG. 1 is a case of a simple model that takes into account electrolyte resistance $R_s$, interface resistance $R_{int}$ including charge transfer resistance and film resistance, capacitance C of an electric double layer incidental to the charge transfer resistance, the film resistance, and the like, and diffusion $Z_w$ of a charge carrier. That is, an electrochemical reaction of a simple system in an electrochemical cell in which a reference electrode is used is configured from movement of ions in an electrolyte, a charge transfer reaction on an electrode interface, and diffusion of the ions involved in the charge transfer reaction. Note that, in an electrochemical cell in which a reference electrode is not used, since impedances of two electrodes (a positive electrode and a negative electrode) are included, a locus of a semicircle is an overlapping locus of at least two semicircles. By analyzing the locus using an appropriate equivalent circuit model, characteristics of each of components such as a plurality of electrodes configuring the electrochemical cell and an electrolyte can be grasped.

For example, when the diameter of a semicircle indicating the interface resistance $R_{int}$ increases, this indicates that a change occurs in the electrochemical cell. That is, this indicates that, in a secondary battery, the battery is deteriorated. When the electrochemical cell is a lithium ion secondary battery, it is surmised that resistance increases because of deterioration of an active material itself such as a change of a crystal structure and because a lithium ion electrolyte component and an organic solvent in the electrolyte decompose and deposit in a form of an organic substance and an inorganic substance on the surfaces of the negative electrode and the positive electrode as electrolyte decomposition products and insertion and desorption of the lithium ions are hindered.

An electric automobile and the like being spread in recent years uses a secondary battery, which is an electrochemical cell, as a power source. However, since costs increases, it is unrealistic to mount frequency characteristic analyzers and potentiostats in respective automobiles in order to evaluate characteristics with the alternating-current impedance method.

To realize a low carbon society, introduction of renewable energy such as solar power generation or wind power generation is in progress. In order to perform stable power supply using the renewable energy, a large power storage system is indispensable.

The large power storage system uses a large-capacity secondary battery as a main component. The large-capacity secondary battery has extremely low internal resistance. Therefore, to evaluate characteristics with the alternating-current impedance method, an extremely expensive large-capacity potentiostat is necessary. For example, when the internal resistance of the secondary battery is 10 mΩ, 300 A is necessary as a signal current of the potentiostat to control a voltage to 3 V. When the internal resistance is 1 mΩ, 3000 A is necessary as the signal current. Voltage control is not easy either.

Note that Japanese Patent Application Laid-Open Publication No. 2003-090869 discloses a measurement apparatus that applies, to a battery, a signal superimposed with sine waves having a plurality of frequencies and Fourier-transforms a response signal to acquire impedance at the plurality of frequencies.

Japanese Patent Application Laid-Open Publication No. 2012-185167 discloses that, in a power storage apparatus including a plurality of batteries, a pseudo sine wave signal is applied from one battery to the other batteries to measure impedance.

On the other hand, an embodiment of the present invention has an object of providing an electrochemical analysis apparatus having a simple configuration that can acquire impedance characteristics of an electrochemical cell and an electrochemical system including electrochemical analysis apparatus.

DISCLOSURE OF INVENTION

Means for Solving the Problem

An electrochemical analysis apparatus according to an embodiment of the present invention includes: a power controller that generates a rectangular wave signal having a first frequency and applies the rectangular wave signal to an electrochemical cell including a plurality of electrodes and an electrolyte; a Fourier transform section that Fourier-transforms a response signal of the electrochemical cell to the rectangular wave signal and calculates frequency characteristics including a component of a second frequency of an integer multiple of the first frequency; and a calculating section that calculates an impedance characteristic of the electrochemical cell based on the frequency characteristics calculated by the Fourier transform section.

An electrochemical system according to another embodiment of the present invention includes: an electrochemical cell including a plurality of electrodes and an electrolyte; and an electrochemical analysis apparatus including: a power controller that generates a rectangular wave signal having a first frequency and applies the rectangular wave signal to the electrochemical cell; a Fourier transform section that Fourier-transforms a response signal of the electrochemical cell to the rectangular wave signal and calculates frequency characteristics including a component of a second frequency of an integer multiple of the first frequency; and a calculating section that calculates an impedance characteristic of the electrochemical cell based on the frequency characteristics calculated by the Fourier transform section.

BEST MODE FOR CARRYING OUT THE INVENTION

First Embodiment

Figure 2:
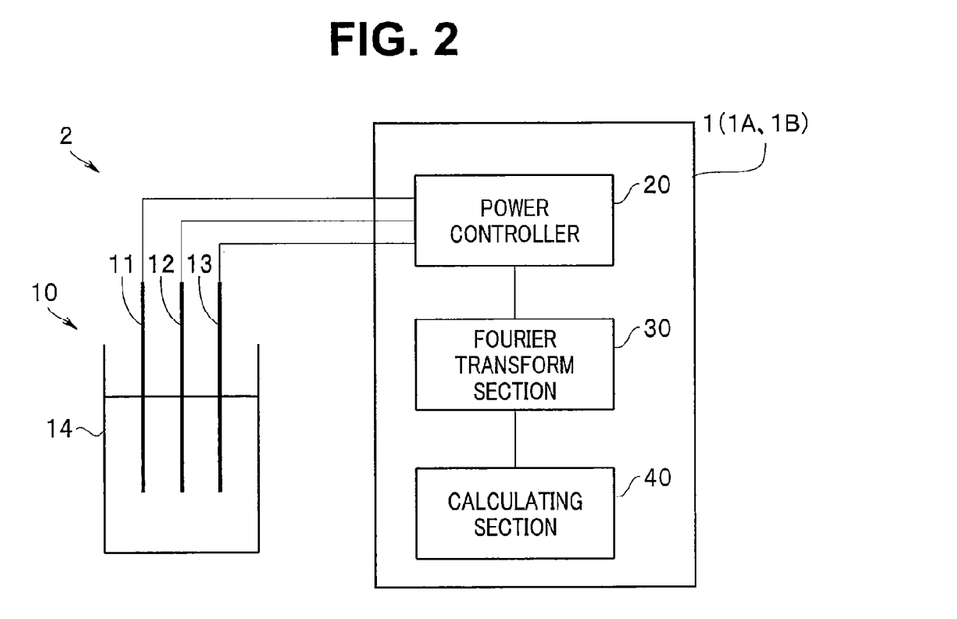
FIG. 2 is a configuration diagram of an electrochemical system in a first embodiment.

As shown in FIG. 2, an electrochemical system 2 in a first embodiment includes an electrochemical cell 10 and an electrochemical analysis apparatus 1. The electrochemical analysis apparatus 1 includes a power controller 20 that generates a signal applied to the electrochemical cell 10, a Fourier transform section 30, and a calculating section 40.

The electrochemical system 2 is a system for analyzing an oxidation-reduction reaction of hexacyanoferrate. The electrochemical cell 10 includes a working electrode (WE) 11 formed of glassy carbon, a counter electrode (CE) 12 formed of a platinum wire, a reference electrode (RE) 13 formed of silver/silver chloride and 3M-NaCl, and an electrolyte 14. The electrolyte 14 is a water solution including 5 mM of $K_4[Fe(CN)_6]$, 5 mM of $K_3[Fe(CN)_6]$, and 0.5 M of $KNO_3$.

The power controller 20 generates a rectangular wave signal of a voltage having a first frequency f1 with reference to the reference electrode (RE) 13 and applies the rectangular wave signal to the working electrode (WE) 11 and the counter electrode (CE) 12 of the electrochemical cell 10. The power controller 20 may use a signal based on an electrode current instead of the voltage. The power controller 20 may generate the rectangular wave signal with reference to the counter electrode (CE) without using the reference electrode (RE) 13 and apply the rectangular wave signal to the working electrode (WE) 11 and the counter electrode (CE) 12 of the electrochemical cell 10. The power controller 20 may apply a rectangular wave of an electric current. The power controller 20 that outputs a simple rectangular wave signal may be configured by, for example, simply combining, with a direct-current power supply, an ON/OFF switch that operates at a predetermined cycle.

The Fourier transform section 30 is an arithmetic circuit that Fourier-transforms a response signal of the electrochemical cell 10 to the rectangular wave signal applied by the power controller 20 and calculates frequency characteristics (spectra of an input signal and an output signal) including components of a second frequency (3f1, 5f1, 7f1, . . . ) of an odd multiple of a first frequency (f1). The calculating section 40 is an arithmetic circuit that calculates impedance characteristics including impedances and phase differences at a plurality of frequencies of the electrochemical cell 10 based on input and output spectra calculated by the Fourier transform section 30. The Fourier transform section 30 and the calculating section 40 may be an integral circuit, for example, a central processing unit (CPU) that also performs control of the entire electrochemical system 2.

Figure 3:
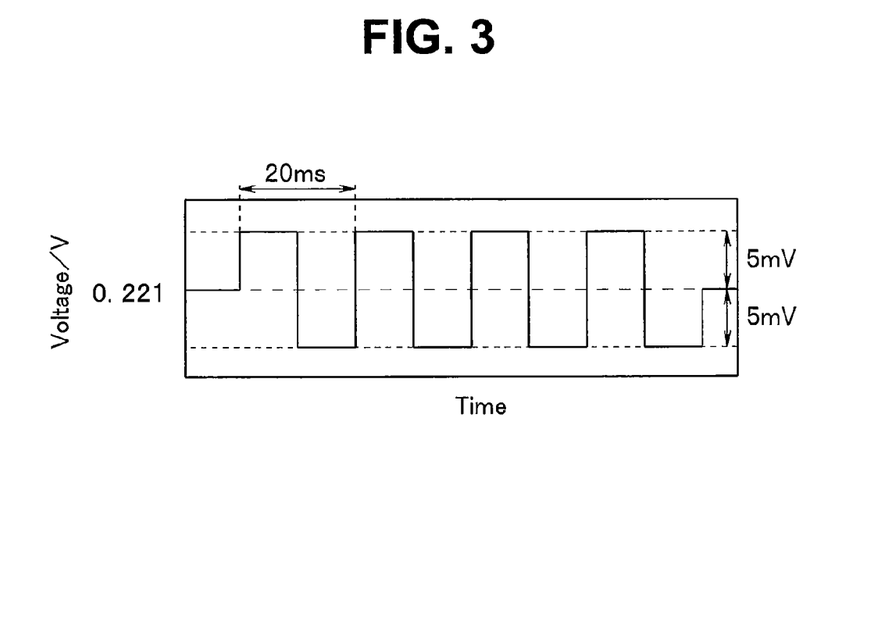
FIG. 3 is a diagram showing a rectangular wave signal generated by a power controller of the electrochemical system in the first embodiment.

FIG. 3 shows a rectangular wave signal having a first frequency (f1=50 Hz) outputted by the power controller 20. Midpoint potential is 0.221 V vs. Ag/AgCl of potential (immersion potential) between the working electrode (WE) 11 and the reference electrode (RE) 13 at a time when a signal is not applied. Voltage amplitude is 10 mV.

Figure 4:
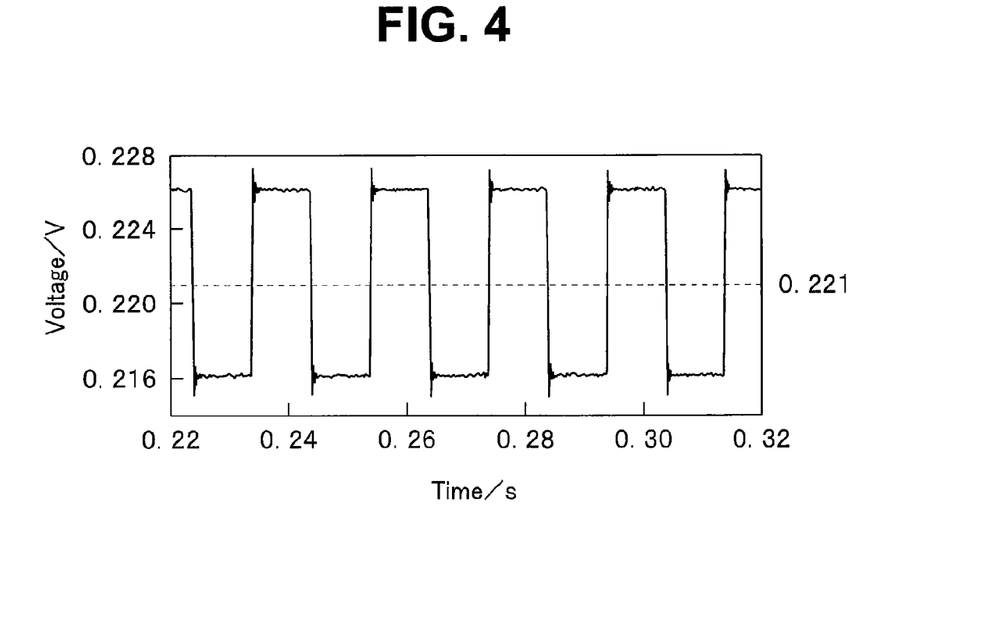
FIG. 4 is a diagram showing a response signal (voltage) of an electrochemical cell of the electrochemical system in the first embodiment.
Figure 5:
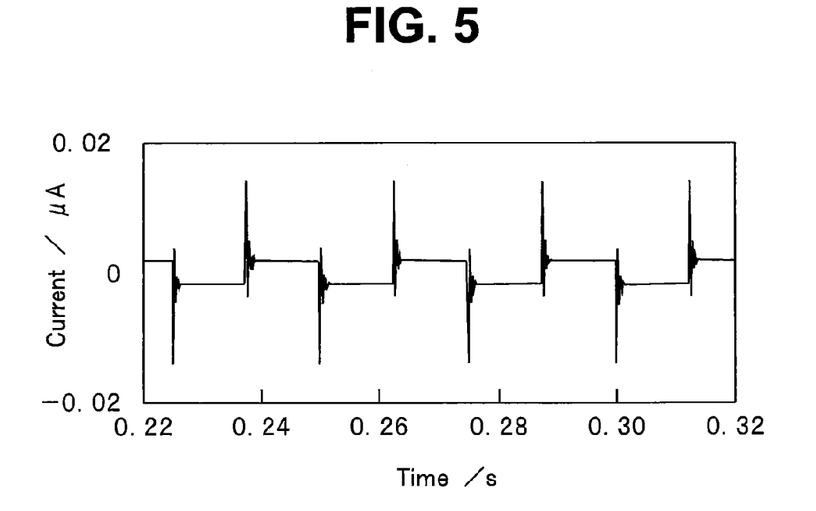
FIG. 5 is a diagram showing a response signal (electric current) of the electrochemical cell of the electrochemical system in the first embodiment.
Figure 6:
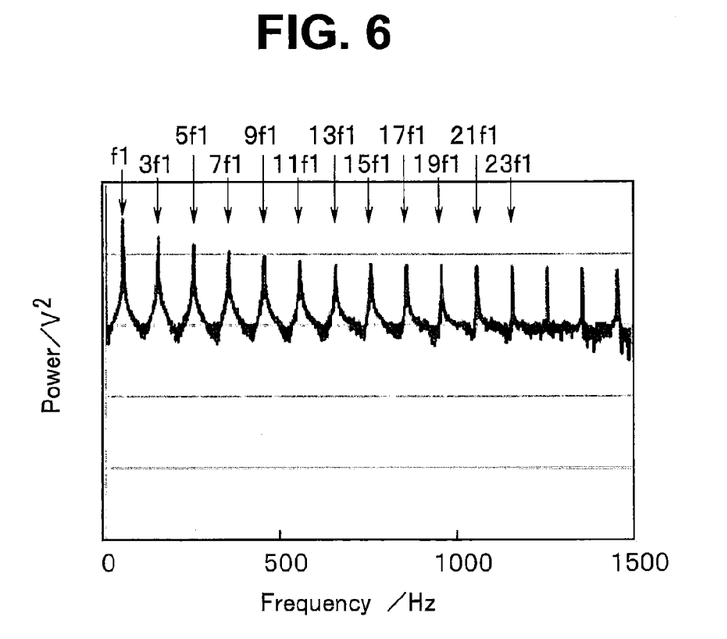
FIG. 6 is a diagram showing a spectrum (power spectrum notation) obtained by Fourier-transforming the response signal (voltage) of the electrochemical cell of the electrochemical system in the first embodiment.
Figure 7:
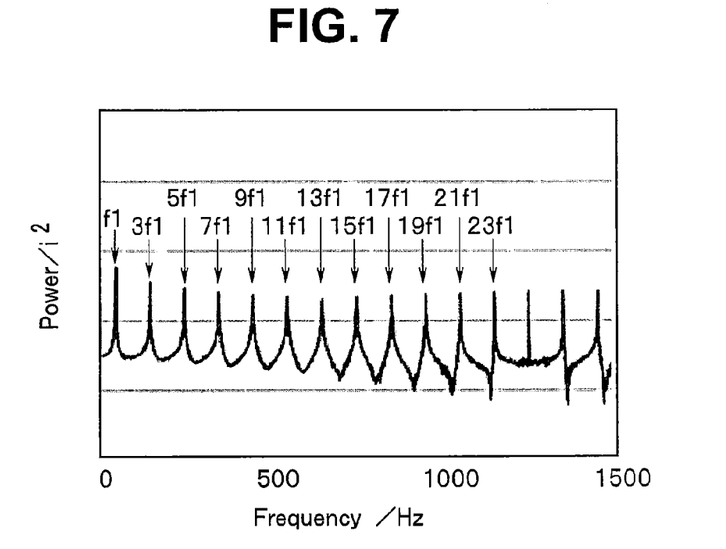
FIG. 7 is a diagram showing a spectrum (power spectrum notation) obtained by Fourier-transforming the response signal (electric current) of the electrochemical cell of the electrochemical system in the first embodiment.

FIG. 4 and FIG. 5 show a response signal of the electrochemical cell 10 to the rectangular wave signal. FIG. 6 and FIG. 7 show input and output spectra (power spectrum notation) calculated from the response signal by the Fourier transform section 30.

As shown in FIG. 6 and FIG. 7, in the power spectra calculated by the Fourier transform section 30, in addition to peaks of the first frequency (f1=50 Hz), peaks of the second frequency (3f1=150 Hz to 23f1=1150 Hz) of an odd multiple of the first frequency (f1) are included. That is, by applying the rectangular wave signal having the first frequency (f1), components of a plurality of second frequencies (f2) higher than the first frequency (f1) are acquired.

Figure 8A:
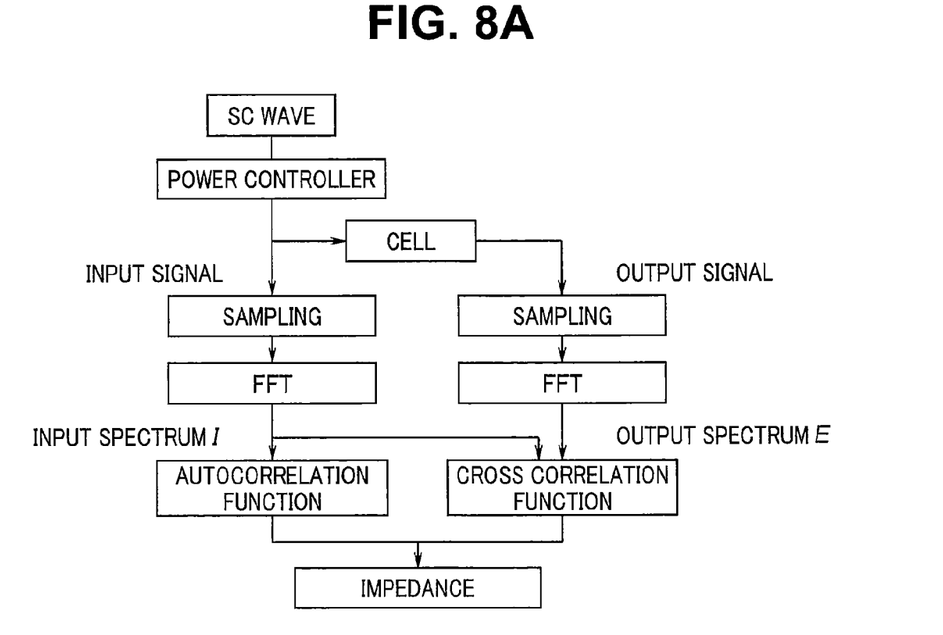
FIG. 8A is a diagram for explaining a method of calculating impedances from input and output spectra calculated by a Fourier transform section.

FIG. 8A is a flowchart for calculating impedances (Z', Z") at frequencies of the calculating section 40 at a time when a current rectangular wave is used. A created rectangular wave signal is applied to the electrochemical cell using the power controller, an input signal current and an output signal voltage are sampled, and an input spectrum I and an output spectrum E are obtained by Fourier transform of obtained data. From a cross correlation function and an autocorrelation function of the spectra at that point, the impedances (Z', Z") at the respective frequencies are calculated according to the cross correlation function/the autocorrelation function.

Figure 8B:
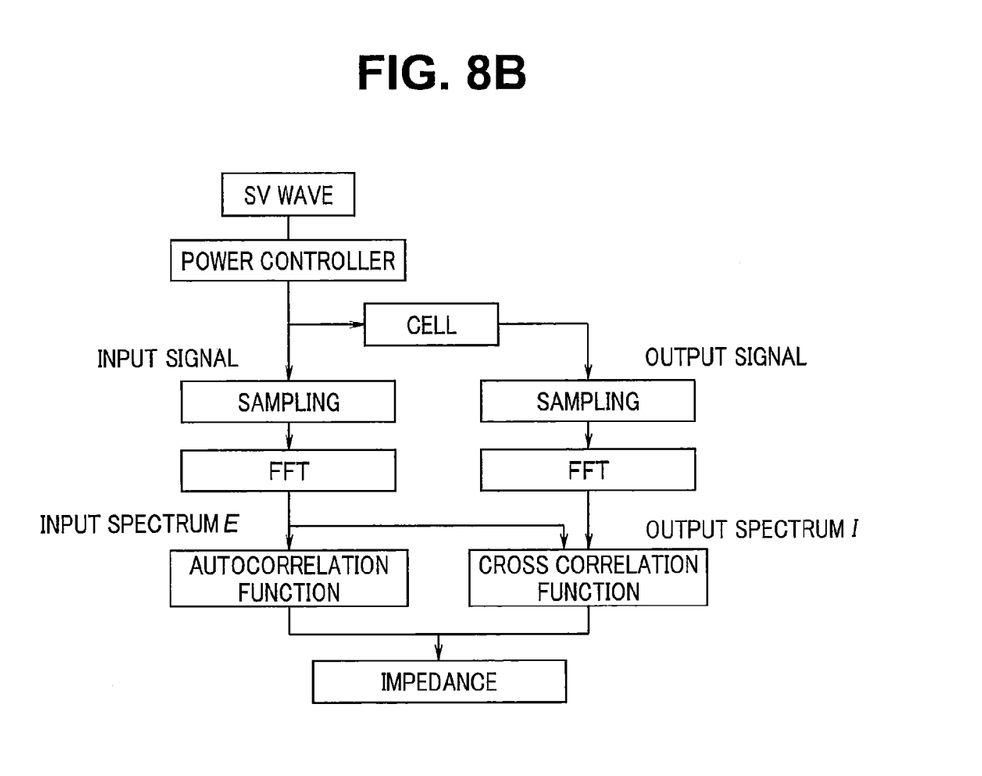
FIG. 8B is a diagram for explaining the method of calculating impedances from the input and output spectra calculated by the Fourier transform section.

FIG. 8B is a flowchart for calculating the impedances (Z', Z") at the frequencies of the calculating section 40 at a time when a voltage rectangular wave is used. A created rectangular wave signal is applied to the electrochemical cell using the power controller, an input signal voltage and an output signal current are sampled, and an input spectrum E and an output spectrum I are obtained by Fourier transform of obtained data. From a cross correlation function and an autocorrelation function of the spectra at that point, the impedances (Z', Z") at the respective frequencies are calculated according to the autocorrelation function/the cross correlation function.

Figure 9:
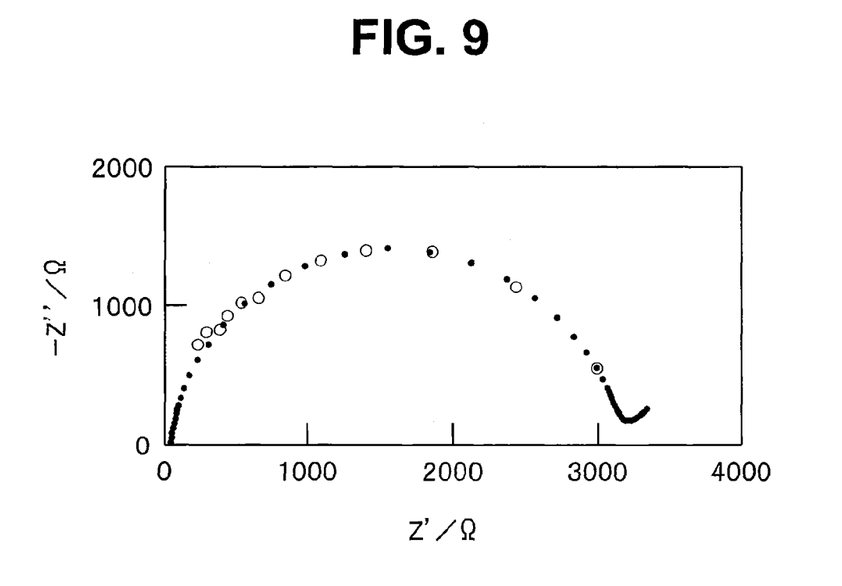
FIG. 9 is a diagram showing a Nyquist plot of the electrochemical system in the first embodiment.

FIG. 9 is a Nyquist plot of the electrochemical cell 10. White circles indicate impedances based on the first frequency (f1=50 Hz) and eleven kinds of the second frequencies f2 (3f1=150 Hz to 23f1=1150 Hz) of the input and output spectra calculated by the Fourier transform section 30. Black circles indicate impedances acquired by a normal alternating-current impedance method. Note that, in the normal alternating-current impedance method, frequencies of a sine wave (voltage amplitude: 10 mV) were scanned from 100 kHz to 1 Hz using a frequency characteristic analyzer and a potentiostat.

As shown in FIG. 9, the Nyquist plot obtained by the electrochemical system 2 in the embodiment and the Nyquist plot obtained by the normal alternating-current impedance method coincide with each other very well.

As it is evident from the above result, although the electrochemical system 2 has a simple configuration not including a frequency characteristic analyzer and a potentiostat, the electrochemical system 2 can acquire an impedance characteristic of the electrochemical cell 10 same as an impedance characteristic obtained by the alternating-current impedance method. By analyzing the acquired impedance characteristic using an equivalent circuit model, it is possible to grasp characteristics and the like for each of the components such as the electrodes and the electrolyte configuring the electrochemical cell 10.

Note that intensity of the second frequency of n multiple of the first frequency in the input and output spectra calculated by the Fourier transform section 30 is 1/n of intensity of the first frequency. Therefore, it is difficult to acquire high-frequency components in a system with a lot of noise components. For example, in the power spectrum shown in FIG. 7, components of frequencies higher than the frequency 23f1 have large variation and lack reliability. Therefore, the components cannot be used for an analysis in which an equivalent circuit model is used.

Even when components of the second frequency (3f1) of three times of at least one frequency (f1) are only acquired, that is, in a Nyquist plot including data at two points, an analysis is not impossible. It is preferable that components of a plurality of second frequencies (f2) are included in the input and output spectra calculated by the Fourier transform section 30. It is particularly preferable that components of three or more second frequencies (f2) are included in the input and output spectra.

Note that, in the electrochemical system 2, when the first frequency (f1) is 5 to 50 Hz, a frequency (23f3) of twenty-three times of the first frequency f1 was able to be acquired as the second frequency f2. That is, impedances at twelve kinds of frequencies in total were able to be acquired. On the other hand, at f1=250 Hz, the second frequency f2 was able to be acquired up to 7f1. At f1=500 Hz, the second frequency f2 was able to be acquired only by 3f1.

In order to stably obtain an impedance response based on the second frequency f2, measurement at a high sampling rate is preferable. As a sampling rate is higher, measurement of a high frequency f2 is easier. The sampling rate is more preferably 100 times or more of the first frequency f1.

At f1 at a high frequency, noise tends to occur in a portion where polarity of an electric current reverses in the power controller 20. When noise occurs, it is preferable to offset potential or a current value to prevent the polarity of the electric current from reversing.

That is, the power controller 20 of the electrochemical analysis apparatus 1 can use a direct-current power supply more inexpensive than an alternating-current power supply. Further, the power controller 20 that generates a direct-current rectangular wave may have a simple configuration for simply ON/OFF-controlling a signal of predetermined potential or a predetermined current value.

When a current value in the power controller 20 is near 0, a current waveform different from a region where a sufficient electric current value is obtained is sometimes shown. In such a case, it is preferable to offset a voltage or a current value to prevent an electric current from decreasing to zero.

Only components of the frequency (3f1, etc.) of an odd multiple of the first frequency (f1) were included in the input and output spectra calculated by the Fourier transform section 30. On the other hand, when the first frequency (f1) is higher, because of an influence of response speed of the cell 10, a frequency (2f1, 4f1, . . . ) of an integer multiple of the first frequency (f1) is sometimes included.

That is, components of a frequency of an integer multiple of the first frequency (f1) may be included in the input and output spectra calculated by the Fourier transform section 30.

The rectangular wave signal outputted by the power controller 20 is not limited to a waveform having an extremely steep rising edge. The rectangular wave signal outputted by the power controller 20 is also regarded as a so-called saw-tooth wave that changes at a certain gradient when a frequency is increased. The rectangular wave signal outputted by the power controller 20 is not limited to a waveform having an extremely steep rising edge and an extremely steep falling edge. The rectangular wave signal outputted by the power controller 20 is also regarded as a so-called triangular wave that changes at a certain gradient when a frequency is increased. That is, the rectangular wave in the present embodiment is a concept including the saw-tooth wave and the rectangular wave.

Further, the rectangular wave signal outputted by the power controller 20 may be actively changed to a saw-tooth wave signal using a delay circuit such as an LC circuit.

In the saw-tooth wave, the triangular wave, and the like, components of a frequency of an integer multiple of the first frequency (f1) are included in the input and output spectra calculated by the Fourier transform section 30.

Modification 1 of the First Embodiment

In an electrochemical analysis apparatus 1A (an electrochemical system 2A) in this modification, the power controller 20 applies a signal having a third frequency (f3) lower than the first frequency (f1) formed by a rectangular wave signal of the first frequency (f1). A Fourier transform section calculates input and output spectra including components of the third frequency (f3).

The Fourier transform section 30 calculates input and output spectra including components of the first frequency (f1) of the rectangular wave signal, components of a frequency (3f1, 5f1, 7f1, . . . ) of an odd multiple of the first frequency (f1), and components of the third frequency (f3) lower than the first frequency (f1). Further, components of a frequency of an odd multiple of the third frequency (f3) is also included in the input and output spectra.

Figure 10:
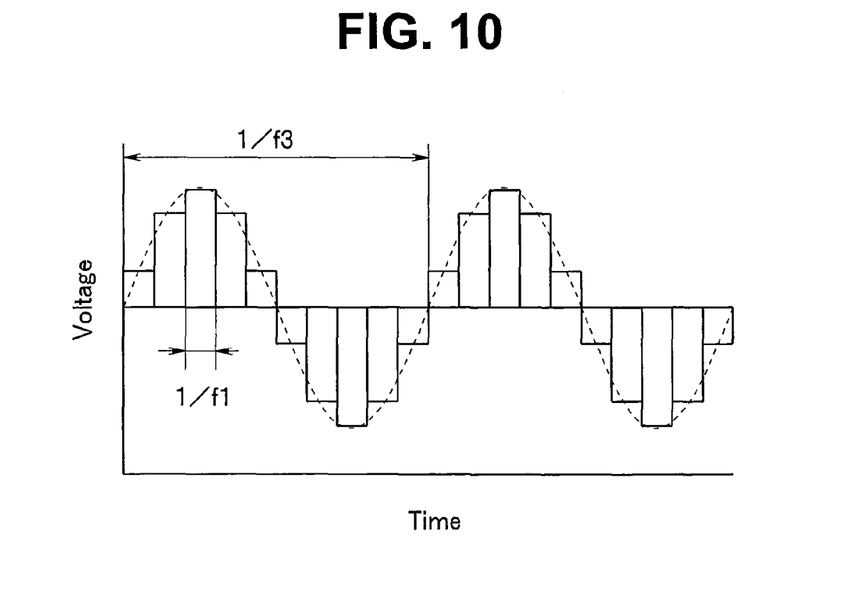
FIG. 10 is a diagram showing a rectangular wave signal of an electrochemical system in a modification 1 of the first embodiment.

For example, as shown in FIG. 10, the power controller 20 generates a pseudo sine wave signal having the third frequency (f3) lower than the first frequency (f1) formed by the rectangular wave signal having the first frequency (f1).

In addition to the effects of the electrochemical analysis apparatus 1 (the electrochemical system 2), the electrochemical analysis apparatus 1A (the electrochemical system 2A) can also detect frequency components based on the third frequency (f3). Therefore, accuracy of an impedance analysis is higher.

Figure 11:
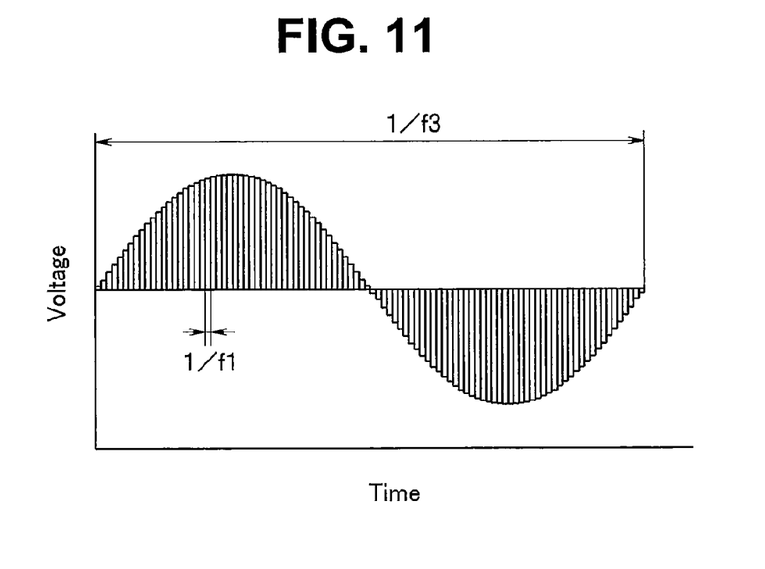
FIG. 11 is a diagram showing a rectangular wave signal of the electrochemical system in the modification 1 of the first embodiment.

Note that, as shown in FIG. 11, for example, when the first frequency (f1) is sufficiently higher than the third frequency (f3), a pseudo sine wave can be regarded as a sine wave. That is, when impedance of a low frequency wave is acquired, the power controller 20 can also be used as a sine wave generating apparatus.

Depending on a bipolar function of the power controller 20, when a pseudo waveform is an alternating-current waveform, noise sometimes occurs when a positive voltage is switched to a negative voltage and when the negative voltage is switched to the positive voltage. Depending on the bipolar function of the power controller 20, when a pseudo waveform is an alternating-current waveform, noise sometimes occurs when a positive current is switched to a negative current and when the negative current is switched to the positive current. When it is not desired to cause noise, it is preferable to offset a voltage or a current value to prevent polarity of a voltage or an electric current from reversing.

Note that, by further reducing the third frequency (f3), it is also possible to analyze diffusion $Z_w$ of a charge carrier, that is, Warburg impedance from a Nyquist plot.

Modification 2 of the First Embodiment

In an electrochemical analysis apparatus 1B (an electrochemical system 2B) in this modification, the power controller 20 applies rectangular wave signals having a plurality of first frequencies f1A and f1B. The Fourier transform section 30 calculates input and output spectra including components of third frequencies respectively of an odd multiple of the plurality of first frequencies.

Figure 12:
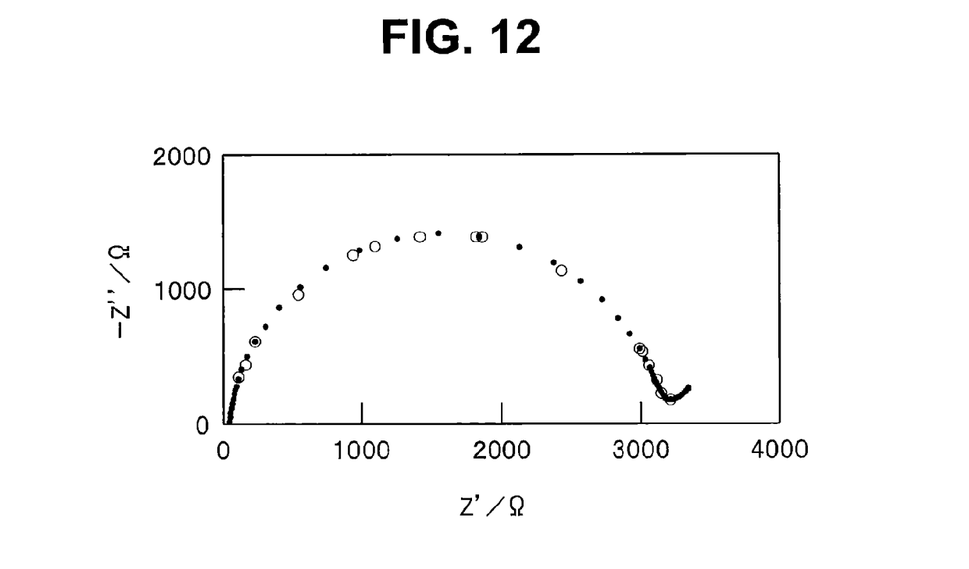
FIG. 12 is a diagram showing a Nyquist plot of an electrochemical system in a modification 2 of the first embodiment.

FIG. 12 is a Nyquist plot of the electrochemical cell 10 in which data acquired from input and output spectra calculated by the Fourier transform section 30 when the power controller 20 outputs rectangular wave signals having four kinds of first frequencies of fA1=5 Hz, fB1=50 Hz, fC1=250 Hz, and fD1=500 Hz in order are plotted by white circles. Black circles are data acquired by the normal alternating-current impedance method same as the data in FIG. 9.

That is, the impedances Z', Z'' at sixteen kinds of frequencies in total of f1A=5 Hz, 3f1A=15 Hz, 5f1A=25 Hz, 7f1A=35 Hz, 9f1A=45 Hz, f1B=50 Hz, 3f1B=150 Hz, 5f1B=250 Hz, 7f1B=350 Hz, 9f1B=450 Hz, f1C=250 Hz, 3f1C=750 Hz, 5f1C=1250 Hz, 7f1C=1750 Hz, f1D=500 Hz, and 3f1D=1500 Hz were acquired from the input and output spectra.

In addition to the effects of the electrochemical analysis apparatus 1 (the electrochemical system 2), the electrochemical analysis apparatus 1B (the electrochemical system 2B) in this modification can acquire impedances at high accuracy at a larger number of frequencies.

Note that it is preferable to set frequencies of a plurality of rectangular wave signals outputted by the power controller 20 such that frequencies of an odd multiple of the frequencies are not the same. That is, when the frequencies of an odd multiple of the frequencies of the plurality of rectangular wave signals are the same, an impedance analysis sometimes becomes unstable because of an error of components acquired at the frequencies. Further, by setting the frequencies not to be the same, it is possible acquire impedances at a larger number of frequencies.

Second Embodiment

Figure 13:
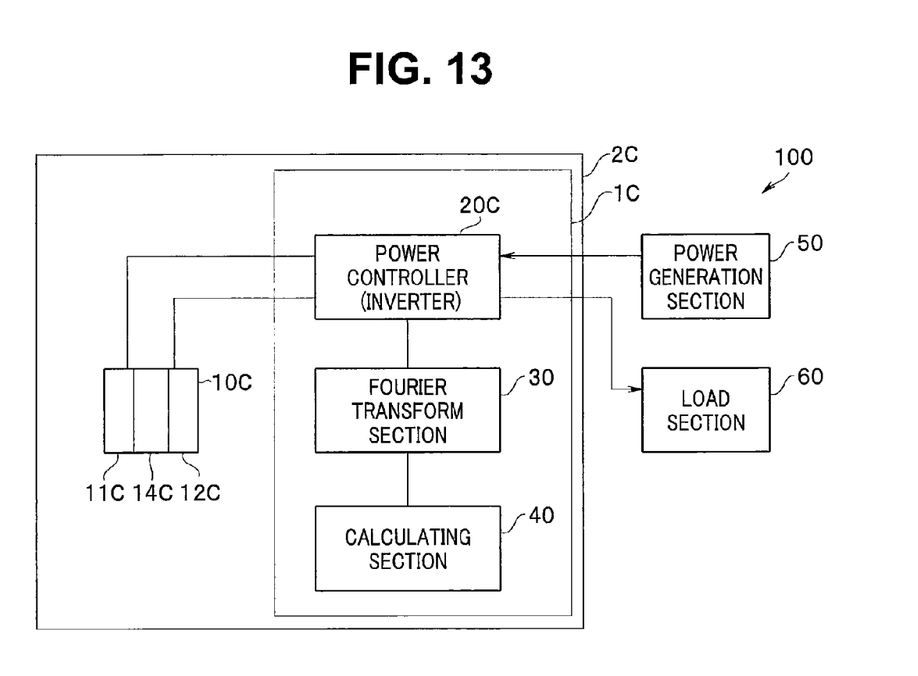
FIG. 13 is a configuration diagram of an electrochemical system in a second embodiment.

As shown in FIG. 13, an electrochemical analysis apparatus 1C (an electrochemical system 2C) in a second embodiment is similar to the electrochemical analysis apparatus 1 (the electrochemical system 2) in the first embodiment in a basic configuration. Therefore, explanation of components having the same functions is omitted.

In the electrochemical system 2C, an electrochemical cell 10A is a large-capacity secondary battery (hereinafter referred to as "battery") 10C. A power controller 20C is called inverter by those skilled in the art. The battery 10C is, for example, a lithium ion battery including a positive electrode 11C containing lithium cobalt oxide and the like, a negative electrode 12C containing a carbon material and the like, and an electrolyte 14C in which $LiPF_6$ is dissolved in cyclic and chain carbonates. Note that the electrochemical cell 10A may be a power storage section that can temporarily store electricity.

The electrochemical system 2C is a large power storage system of a power system 100. In the power system 100, when a generated power amount from a power generation section 50 such as a wind power generation section or a solar power generation section is insufficient for a power consumption amount of a load section 60 in a factory, a home, or the like, electric power is supplied from the battery 10C of the electrochemical system 2C to the load section 60. On the other hand, when the generated power amount exceeds the power consumption amount, the battery 10C is charged.

Note that, when the electrochemical system 2C is a power storage system of an electric automobile, a motor is the power generation section 50 and the load section 60. That is, when electric power is supplied, the motor is driven and power generation is also performed using rotation of the motor.

Figure 14:
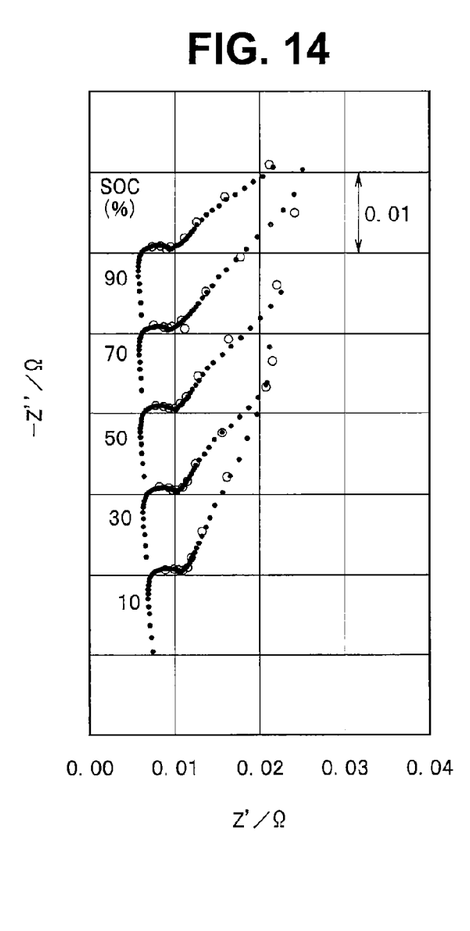
FIG. 14 is a diagram showing a Nyquist plot of the electrochemical system in the second embodiment.
Figure 15:
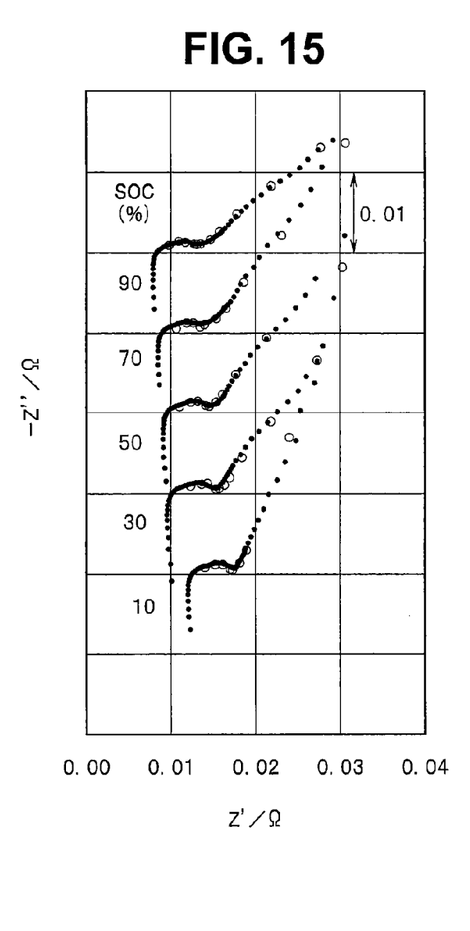
FIG. 15 is a diagram showing a Nyquist plot of the electrochemical system in the second embodiment.

FIG. 14 and FIG. 15 are Nyquist plots in which impedance characteristics of the battery 10C acquired by the electrochemical system 2C are indicated by white circles and impedance characteristics acquired by the normal alternating-current impedance method are indicated by black circles. Five kinds of Nyquist plots obtained when a state of charge (SOC) of the battery 10C is 90% to 10% are shown. FIG. 14 is a Nyquist plot of a new battery 10. FIG. 15 is a Nyquist plot after a charge and discharge test was performed 200 cycles (a deteriorated battery).

Note that, in the electrochemical system 2C, the power controller 20C applied a signal of a rectangular wave signal having 50 Hz (an offset current=0.5 A, amplitude±0.5 A) to the battery 10. In the normal alternating-current impedance method, a frequency having a sine wave (an offset current=0.5 A, amplitude±0.5 A) was scanned from 100 kHz to 1 Hz using a frequency characteristic analyzer and a large-capacity potentiostat. However, since internal resistance of the battery 10C is extremely low at 10 mΩ, measurement by the normal alternating-current impedance method was not easy.

From FIG. 14 and FIG. 15, an impedance characteristic of the battery 10C acquired by the electrochemical system 2C well coincides with an impedance characteristic acquired by the normal alternating-current impedance method. That is, in the electrochemical system 2C in which the electrochemical cell is the battery 10, effects same as the effects of the electrochemical system 2 in the first embodiment are obtained. Further, internal resistance of the battery 10C is extremely low at 10 mΩ, acquisition of an impedance characteristic was easy in the electrochemical system 2C.

FIG. 15 indicates that a diameter ($R_{int}$) of a semicircle increases from the diameter shown in FIG. 14 and the internal resistance increases. That is, the calculating section 40 can further quantitatively detect deterioration of the battery 10C from the impedance characteristic. The calculating section 40 can also separately detect deterioration degrees of the positive electrode 11C, the negative electrode 12C, and the electrolyte by analyzing the positive electrode 11C, the negative electrode 12C, and the electrolyte using an equivalent circuit. Further, the calculating section 40 can also detect a state of charge of the battery 10C in a state in which deterioration of the battery 10 does not change.

In the electrochemical system 2C, acquisition of an impedance characteristic is easy even if internal resistance of a battery is 10 mΩ or less. Further, acquisition of an impedance characteristic is easy even in a battery having internal resistance of 1 mΩ or less in which it is extremely difficult to perform measurement with the normal alternating-current impedance method.

Figure 16A:
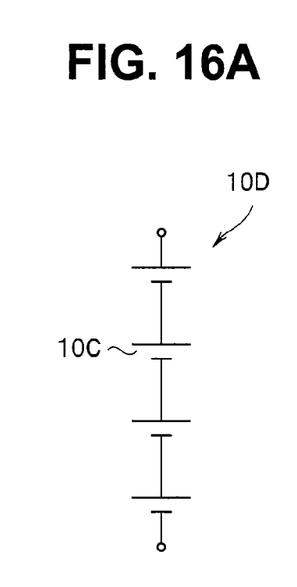
FIG. 16A is a diagram showing a battery unit of an electrochemical system in an embodiment.

To simplify explanation, the electrochemical system 2C includes one battery 10C as the electrochemical cell. However, even if the electrochemical cell is a battery unit 10D in which a plurality of batteries 10C are connected in series shown in FIG. 16A, a battery unit 10E in which the plurality of batteries 10C are connected in parallel shown in FIG. 16B, or a battery unit 10F in which the plurality of batteries 10C are connected in series and in parallel shown in FIG. 16C, by applying a signal to the electrochemical cell, it is also possible to detect a characteristic change of the entire battery unit 10E including the plurality of batteries 10C.

Figure 16B:
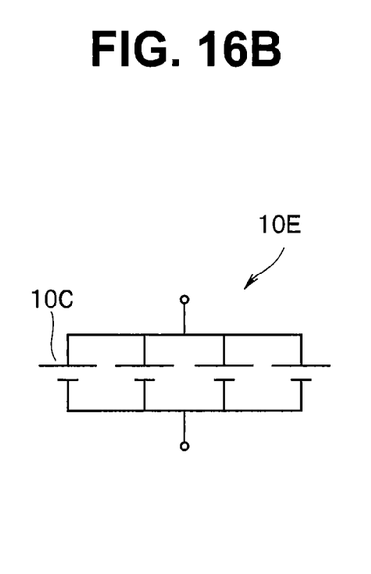
FIG. 16B is a diagram showing a battery unit of an electrochemical system in an embodiment.
Figure 16C:
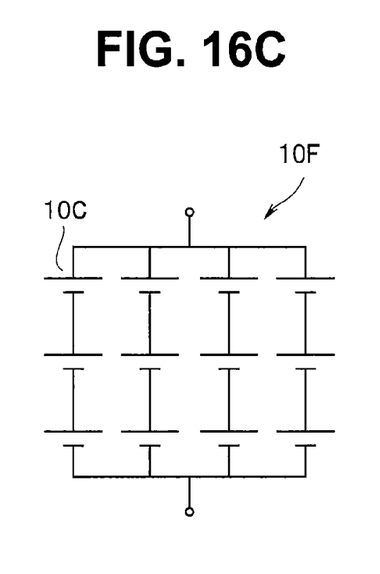
FIG. 16C is a diagram showing a battery unit of an electrochemical system in an embodiment.

In particular, internal resistance of the battery units 10E and 10F in which batteries are connected in parallel is lower than internal resistance of the respective batteries 10C. However, with the electrochemical system 2C, it is easy to acquire an impedance characteristic.

Further, the electrochemical cell is not limited to the lithium secondary battery as long as the electrochemical cell is a power storage device that can store electricity. Various secondary batteries and capacitors can also be used.

The present invention is not limited to the embodiments and the like explained above. Various changes and alterations, for example, combinations of the components in the embodiments are possible in a range in which the gist of the present invention is not changed.

This application is based upon and claims the benefit of priority from Japanese Patent Application No. 2012-285550 filed in Japan on Dec. 27, 2012, the disclosed contents of which are incorporated in the specification, the claims, and the drawings.

The invention claimed is:

1. An electrochemical analysis apparatus for analyzing a secondary battery comprising a plurality of electrodes and an electrolyte, wherein the electrochemical analysis apparatus comprises:

a power controller configured to generate a direct-current rectangular wave signal having a first frequency and continuously apply the direct-current rectangular wave signal to the secondary battery; and a processor comprising hardware, wherein the processor is configured to:
Fourier-transform a response signal of the secondary battery to the direct-current rectangular wave signal;
calculate frequency characteristics comprising components of a plurality of second frequencies of integer multiples of the first frequency;
calculate impedances of the secondary battery at the first frequency and the plurality of second frequencies based on the frequency characteristics calculated;
create a Nyquist plot based on the impedances at the first frequency and the plurality of second frequencies; and
detect a change in the Nyquist plot.

2. The electrochemical analysis apparatus according to claim 1,
wherein each of the plurality of second frequencies is a frequency of an odd multiple of the first frequency.

3. The electrochemical analysis apparatus according to claim 2,
wherein the power controller is configured to apply, to the secondary battery, a signal that has a third frequency lower than the first frequency and is formed by a plurality of rectangular wave signals having the first frequency, and
wherein the processor is configured to calculate a frequency characteristic including components of the third frequency.

4. The electrochemical analysis apparatus according to claim 2,
wherein the power controller is configured to apply rectangular wave signals having a plurality of frequencies to the secondary battery, and
wherein the processor is configured to calculate a frequency characteristic including components of a frequency of an integer multiple of each of the plurality of frequencies.

5. The electrochemical analysis apparatus according to claim 4,
wherein the frequencies of the plurality of rectangular wave signals are set such that frequencies of an odd multiple of the frequencies are different from one another.

6. An electrochemical system comprising:
the electrochemical analysis apparatus according to claim 2; and
the secondary battery.

7. The electrochemical analysis apparatus according to claim 1,
wherein the power controller is configured to apply the direct-current rectangular wave signal to a battery unit comprising a plurality of the secondary battery connected to one another, and
wherein the processor is configured to detect a characteristic change of the battery unit.

8. The electrochemical analysis apparatus according to claim 1,
wherein internal resistance of the secondary battery is 10 mΩ or less.

* * * * *